United States Patent [19]

Plattier et al.

[11] 3,954,794
[45] May 4, 1976

[54] HETEROCYCLIC COMPOUNDS

[75] Inventors: Marcel Plattier, Antibes; Bernard Shimizu; Paul Jose Teisseire, both of Grasse, all of France

[73] Assignee: Societe Anonyme Roure Bertrand Dupont, Paris, France

[22] Filed: Mar. 18, 1974

[21] Appl. No.: 452,349

[30] Foreign Application Priority Data
Mar. 22, 1973 Switzerland.................... 4301/73

[52] U.S. Cl................. 260/310 R; 260/310 C; 252/522; 260/250 Q; 260/283 R
[51] Int. Cl.².................................... C07D 231/54
[58] Field of Search.................... 260/310 R

[56] References Cited
UNITED STATES PATENTS
3,691,179  9/1972  Lucas et al............. 260/310 R
3,691,180  9/1972  Blatter et al............ 260/310 R

*Primary Examiner*—Donald B. Moyer
*Attorney, Agent, or Firm*—Wallenstein, Spangenberg, Hattis & Strampel

[57] ABSTRACT

Novel compounds of the formulae I – IV are disclosed. The compounds are useful as odoriferous agents. Processes for the preparation of said compounds are also disclosed.

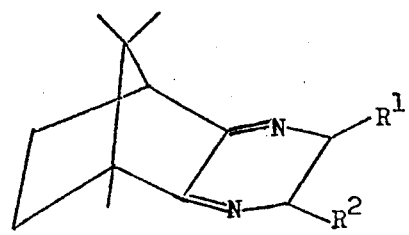

I

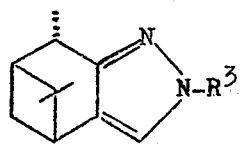

II

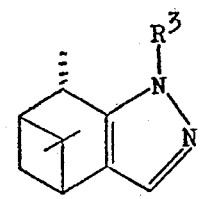

III

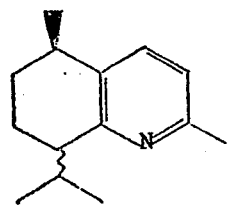

IV

In said formulae $R^1$ and $R^2$ are hydrogen or an alkyl group having 1 to 5 carbons. $R^3$ is alkyl having 1 to 5 carbons.

4 Claims, No Drawings

HETEROCYCLIC COMPOUNDS

DETAILED DESCRIPTION OF THE INVENTION

The present invention is concerned with novel compounds of the formulae I, II, III and IV:

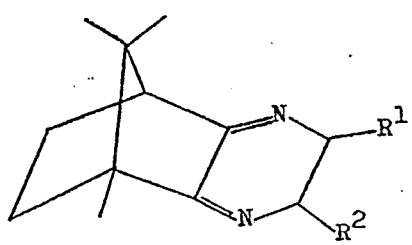

I

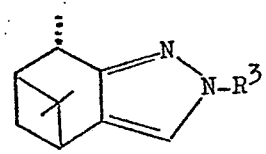

II

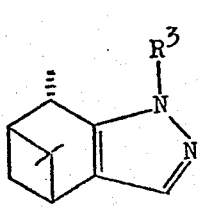

III

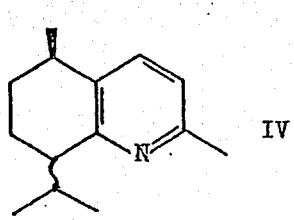

IV wherein $R^1$ and $R^2$, represent hydrogen or an alkyl group having from 1 to 5 carbon atoms, and $R^3$ represents an alkyl group having from 1 to 5 carbon atoms. The alkyl groups preferably contain from 1 to 3 carbon atoms. The alkyl group is preferably methyl. $R^1$ and $R^2$ are preferably both hydrogen or one is hydrogen and the other methyl.

In accordance with the invention, the compounds of the formulae I, II, III and IV are manufactured a. for the manufacture of camphor-2,3-dihydropyrazines of the formula I, by condensing camphorquinone with an α-diamine of the general formula $$H_2N-CHR^1-CHR^2-NH_2 \qquad VI$$

wherein $R^1$ and $R^2$ have the meanings given above, preferably in the presence of an acidic condensation agent such as p-toluenesulphonic acid and an inert organic solvent such as, for example, benzene, or b. for the manufacture of pinanopyrazoles of the formulae II or III, by treating 4-formyl-pinan-3-one of the formula

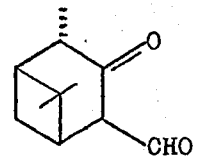

VII with an alkyl hydrazine of the formula $$H_2N-NH-R^3 \qquad VIII$$

wherein $R^3$ has the meaning given above,
or by treating 4-formyl-pinan-3-one of the formula VII with hydrazine and alkylating the so obtained tautomeric compounds of the formulae

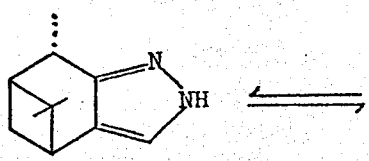

IX

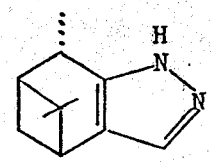

X with a compound yielding the residue R³, for example with a dialkyl sulphate, or c. for the manufacture of 2,5-dimethyl-8-isopropyl-5,6,7,8-tetrahydroquinoline of the formula IV, by treating the dione 1-methyl-4-isopropyl-2-(3'-oxobutyl)-cyclohexan-3-one of the formula

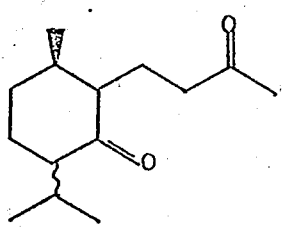

XI with an hydroxylamine salt, preferably with an hydroxylamine hydrohalide such as hydroxylamine hydrochloride.

The dione XI can itself be obtained in a manner known per se from p-menthone (XII) via the enamine XIII,

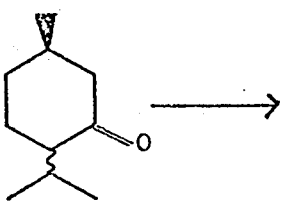

XII

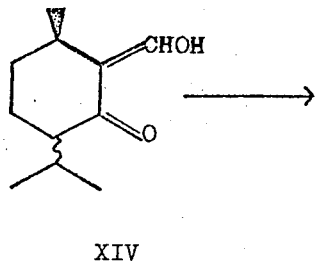 ⟶ XI

XIII for example by the reaction of the ketone XII with pyrrolidine in the presence of an acidic catalyst such as p-toluenesulphonic acid and conversion of the enamine XIII into the dione XI with methylvinyl ketone.

The dione XI can also be obtained according to the following scheme

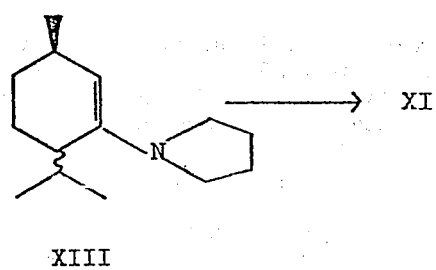

XIV

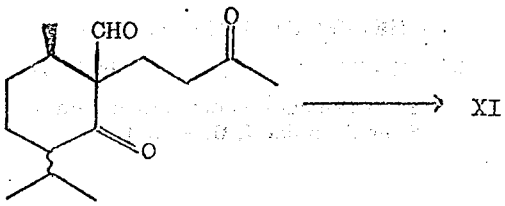 ⟶ XI

XV by the reaction of the hydroxymethylene compound XIV with methylvinyl ketone and subsequent deformylation of the compound XV.

The compounds in accordance with the invention of the formulae I, II, III and IV possess valuable odoriferous properties and can accordingly be used as odorants such as, for example, for the manufacture of odorant compositions such as perfumes. Thus, for example, mixtures of the pinanopyrazoles of the formulae II and III have an amber-like odour. Camphor-2,3-dihydropyrazine (formula I with $R^1$ and $R^2 = H$) has camphoraceous, musty and earthy odour of the patchouli type. Finally, the quinoline derivative of the formula IV has a spicy, slightly amber-like odour with a dry lime note.

The invention will now be illustrated with reference to the following Examples in which all parts are by weight.

EXAMPLE 1

5.6 g [4,3-c]-pinanopyrazole are added to a solution of 2.55 g of sodium hydroxide in 35 ml of water. The mixture is heated to 80°C and then, at this temperature, treated dropwise over 2 hours with 3.85 g of dimethyl sulphate. Subsequently, a further 3.2 g of sodium hydroxide and 12 ml of benzene are added and the mixture is left to stand again for 2 hours at 80°C. Thereupon, the mixture is cooled and extracted with benzene. The solvent is evaporated and the residue distilled in vacuo. There is obtained a mixture consisting of 60% of [4,3-c]pinano-1-methyl-pyrazole and 40% of [4,3-c]-pinano-2-methyl-pyrazole. This mixture has a boiling point of 80° to 82°C/0.2 mm Hg. The separation of the two isomers is effected by preparative gas chromatography.

The starting material can be manufactured as follows:

a. 3.45 g of sodium are added in small pieces to a solution of 22.8 g of isocamphopinone and 16.7 g of ethyl formate in 300 ml of anhydrous diethyl ether. Thereupon, 1 ml of anhydrous ethanol is added dropwise while the temperature is held at 30°C. The mixture is stirred at this temperature for 12 hours and then treated with 3 ml of ethanol. Thereupon, the mixture is stirred for a further 1 hour, then cooled to 0°C and acidified with 50% hydrochloric acid. The product is extracted with diethyl ether, dried over sodium sulphate and the solvent evaporated. The product is distilled in vacuo. It has a boiling point or 79°–80°C/0.6 mm Hg. The yield of 4-formyl-pinan-3-one amounts to 52%.

b. 4 g of hydrazine hydrate are added dropwise to a solution of 12 g of 4-formyl-pinan-3-one in 60 ml of ethanol. During this addition, the temperature is held below 40°C. The mixture is then stirred for 1 hour at room temperature and the methanol evapoated in vacuo. The residue is taken up in 250 ml of 10% hydrochloric acid. The solution is washed with diethyl ether and the aqueous phase made alkaline with ammonia. Thereupon, the mixture is extracted with diethyl ether, the extract dried over sodium sulphate and the solvent evaporated. The residue is fractionated in vacuo and there is obtained [4,3-c]-pinanopyrazole with a boiling point of 104°–106°C. Yield 72%.

EXAMPLE 2

A solution of 15.6 g of camphorquinone, 7.2 g of ethylenediamine and 1 g of p-toluenesulphonic acid in 1 liter of anhydrous benzene is heated at reflux for 3 hours, 1.7 ml of water being produced. The mixture is cooled and washed with 100 ml of a 5 wt.% sodium hydroxide solution. The organic phase is decanted off and the benzene distilled off. The residue is fractionated in vacuo and there is obtained camphor-2,3-dihydropyrazine (formula I: $R^1$ and $R^2 = H$) with a boiling point of 90°–81°C/2.5 mm Hg. $[\alpha]_D = +9.4°$ (ethanol). Yield 72%.

EXAMPLE 3

2 g of 1-methyl-4-isopropyl-2-(3'-oxobutyl)-cyclohexan-3-one, 1.2 g of hydroxylamine hydrochloride and 100 ml of ethanol are added to a 250 ml autoclave. The autoclave is heated at 150°C for 5 hours. Thereupon, the ethanol is distilled off and the residue taken up in 40 ml of 20% potassium hydroxide solution. The mixture is extracted with diethyl ether, the extract dried over sodium sulphate and the ether subsequently distilled off. The residue is purified over a silica gel column (0.05 to 0.2 mm particles) using $CHCl_3$ as the eluant. On distillation, there is obtained 2,5-dimethyl-8-isopropyl-5,6,7,8-tetrahydroquinoline (formula IV) with a boiling point of 70°–72°C/0.4 mm Hg.

The starting material can be manufactured as follows:

a. 77 g of p-menthone, 35 g of pyrrolidine and 0.8 g of p-toluenesulohonic acid are dissolved in 400 ml of anhydrous benzene. The mixture is heated at reflux for 10 hours. At the instant when the further addition of p-toluenesulphonic acid no longer causes further water cleavage, the benzene is distilled off and the residue fractionated in vacuo. The pyrrolidine-enamine of the p-menthone (XIII) is obtained with a boiling point of 80°–82°C. Yield 28%.

b. A mixture of 19.6 g of the pyrrolidine-enamine of p-menthone, 10 ml of methylvinyl ketone and 150 ml of anhydrous benzene is refluxed under nitrogen for 20 hours. The mixture is then cooled and treated with 6 g of sodium acetate in 12 ml of water as well as with 12 ml of acetic acid. The mixture is again refluxed for 4 hours. Then, the product is extracted with benzene and the solvent evaporated. The residue is fractionated in vacuo and there is obtained 1-methyl-4-isopropyl-2-(3'-oxobutyl)-cyclohexan-3-one with a boiling point of 88°–90°C.

Example A (Linden infusion)

| | Parts by weight |
|---|---|
| Hydroxycitronellal | 250 |

Example A-continued (Linden infusion)

| | Parts by weight |
|---|---|
| Crystalline heliotropin | 50 |
| Phenylethyl alcohol | 80 |
| Ionone 100% (5% in ethyl phthalate) | 150 |
| Nonadienal | 150 |
| Violet leaves absolute (1% in ethyl phthalte) | 100 |
| Methylheptyne carbonate (10% in ethyl phthalte) | 20 |
| Ethyl phthalate | 100 |
| 2,5-Dimethyl-8-isopropyl-5,6,7,8-tetrahydroquinoline | 100 |
| | 1000 |

Example B

| | Parts by weight |
|---|---|
| Essence d'armoise | 300 |
| Pepper oil | 250 |
| Coriander oil | 50 |
| Patchouli oil | 100 |
| Lavender oil Laragne 50% | 100 |
| Essence de basilic Colonies | 50 |
| Eugenol | 50 |
| Absolute mousse sylvestre | 250 |
| Vetiver oil Bourbon | 150 |
| Isobutylquinoline | 100 |
| Galaxolide | 100 |
| Camphor-2,3-dihydropyrazine | 500 |
| | 2000 |

Example C (Tobacco base)

| | |
|---|---|
| Ylang-Ylang oil extra | 20 |
| Linalool | 40 |
| Essence de sauge sclaree | 240 |
| Hydroxycitronellal | 400 |
| Methylphenyl acetate | 20 |
| Linalylphenyl acetate | 10 |
| Tonka leaves absolute | 70 |
| Mixture of 1-methyl- and 2-methyl-[4,3-c]-pinano-pyrazole [60:40%] | 200 |
| | 1000 |

We claim:
1. A compound of the formulae II or III

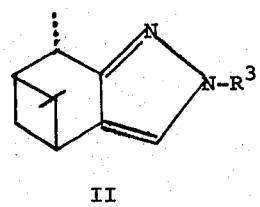

II

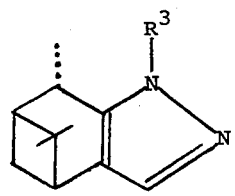

III wherein $R^3$ represents an alkyl group of from 1 to 5 carbon atoms.

2. A compound as claimed in claim 1, wherein $R^3$ represents methyl.

3. [4,3-c]Pinano-1-methyl-pyrazole.

4. [4,3-c]Pinano-2-methyl-pyrazole.

* * * * *